(12) United States Patent
Liu et al.

(10) Patent No.: US 11,382,559 B2
(45) Date of Patent: Jul. 12, 2022

(54) DENTAL SURFACE IMAGING APPARATUS USING LASER PROJECTION

(71) Applicant: Carestream Health, Inc., Rochester, NY (US)

(72) Inventors: Zhaohua Liu, Shanghai (CN); Tan Wang, Shanghai (CN)

( * ) Notice: Subject to any disclaimer, the term of this patent is extended or adjusted under 35 U.S.C. 154(b) by 251 days.

(21) Appl. No.: 15/503,163

(22) PCT Filed: Sep. 16, 2014

(86) PCT No.: PCT/CN2014/086635
§ 371 (c)(1),
(2) Date: Feb. 10, 2017

(87) PCT Pub. No.: WO2016/041147
PCT Pub. Date: Mar. 24, 2016

(65) Prior Publication Data
US 2017/0224272 A1    Aug. 10, 2017

(51) Int. Cl.
*A61B 5/00*     (2006.01)
*A61B 5/107*    (2006.01)
(Continued)

(52) U.S. Cl.
CPC .............. *A61B 5/4547* (2013.01); *A61B 1/24* (2013.01); *A61B 5/0077* (2013.01);
(Continued)

(58) Field of Classification Search
CPC .................. A61B 5/4547; A61B 1/24
See application file for complete search history.

(56) References Cited

U.S. PATENT DOCUMENTS 5,372,502 A   12/1994  Massen et al.
6,885,464 B1   4/2005  Pfeiffer et al.
(Continued)

FOREIGN PATENT DOCUMENTS

CN    102613954        8/2012
CN    107072530 A      8/2017
(Continued)

OTHER PUBLICATIONS

International Search Report dated Jun. 19, 2015 for International Application No. PCT/CN2014/086635, 2 pages.
(Continued)

*Primary Examiner* — Girumsew Wendmagegn

(57) ABSTRACT

An intra-oral imaging apparatus for obtaining a contour image of a tooth has a fringe pattern generator energizable to emit a fringe pattern illumination. The fringe pattern generator has (i) at least one structured light source that is energizable to emit a patterned light beam; (ii) at least one reflective element in the path of the emitted patterned light beam and actuable to rotate about an axis to scan the emitted patterned light beam along a tooth surface as fringe pattern illumination. A detector is configured to acquire one or more images of the fringe pattern illumination from the tooth surface. A control logic processor is configured to control the fringe pattern generator for illuminating the tooth and to obtain and process the one or more images acquired by the detector.

9 Claims, 14 Drawing Sheets

(51) Int. Cl.
  *A61C 9/00* (2006.01)
  *A61B 1/24* (2006.01)
  *G01B 11/25* (2006.01)

(52) U.S. Cl.
  CPC .......... *A61B 5/0088* (2013.01); *A61B 5/1077* (2013.01); *A61B 5/1079* (2013.01); *A61B 5/742* (2013.01); *A61C 9/006* (2013.01); *G01B 11/2513* (2013.01); *G01B 11/2518* (2013.01)

(56) References Cited

U.S. PATENT DOCUMENTS

| | | | |
|---|---|---|---|
| 7,312,924 | B2 | 12/2007 | Trissel |
| 8,577,212 | B2 | 11/2013 | Thiel |
| 2005/0190988 | A1 | 9/2005 | Feron |
| 2007/0086762 | A1 | 4/2007 | O'Keefe et al. |
| 2010/0268069 | A1* | 10/2010 | Liang ............... G06T 7/521 600/425 |
| 2010/0311005 | A1* | 12/2010 | Liang ............... A61B 1/00009 433/29 |
| 2014/0302452 | A1* | 10/2014 | Hack ............... A61B 5/0088 433/29 |

FOREIGN PATENT DOCUMENTS

| | | |
|---|---|---|
| EP | 2 241 247 A1 | 10/2010 |
| EP | 3 193 699 A1 | 7/2017 |
| JP | 2009-518139 A | 5/2009 |
| JP | 2010-246899 A | 11/2010 |
| JP | 2017-533000 A | 11/2017 |
| KR | 10-2017-0058365 A | 5/2017 |
| WO | 2009/139110 A1 | 11/2009 |
| WO | WO 2010/096634 | 8/2010 |
| WO | WO 2010/145669 | 12/2010 |
| WO | WO 2011/145799 | 11/2011 |
| WO | 2016/041147 A1 | 3/2016 |

OTHER PUBLICATIONS

Múnera et al. "Evaluation of Fringe Projection and Laser Scanning for 3D Reconstruction of Dental Pieces Evaluacion De Proyeccion De Franjas Y Escaneo Laser Para La Reconstruccion 3D De Piezas Dentales", Jan. 1, 2012, pp. 65-73, Retrieved from the Internet: URL: http://www.scielo.org.co/pdf/dyna/v79n171/a08v79n171.pdf.
Logozzo et al., "A Comparative Analysis of Intraoral 3d Digital Scanners for Restorative Dentistry", The Internet Journal of Medical Technology, vol. 5, No. 1, Jan. 1, 2008, pp. 1-18.
Extended European Search Report Received for European Patent Application No. 14901983.8, dated Feb. 5, 2018, 18 Pages.
International Preliminary Report on Patentability received for International Application No. PCT/CN2014/086635, dated Mar. 30, 2017, 6 pages.
Communication Pursuant to Rules 70(2) and 70a(2) EPC received for European Application No. 14901983.8, dated Feb. 22, 2018, 1 page.
Notification of Reasons for Refusal received for Japanese Patent Application Serial No. 2017-514283 dated Aug. 14, 2018, 6 pages (including English Translation).

\* cited by examiner

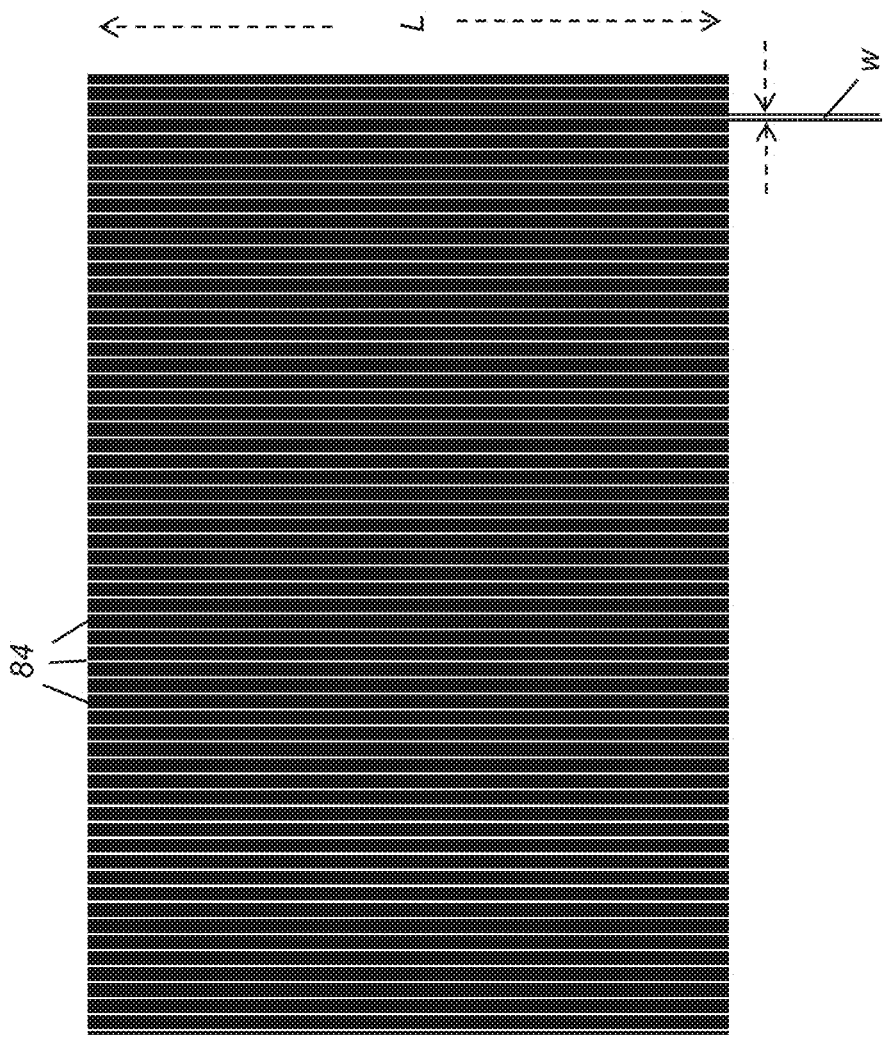

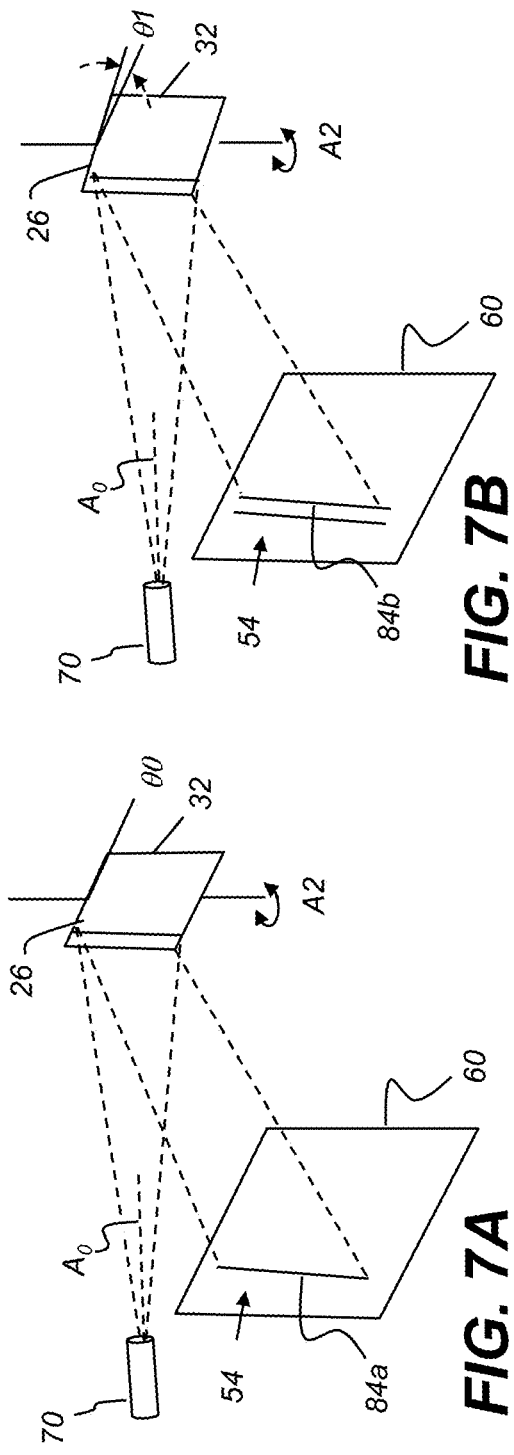
FIG. 7A
FIG. 7B
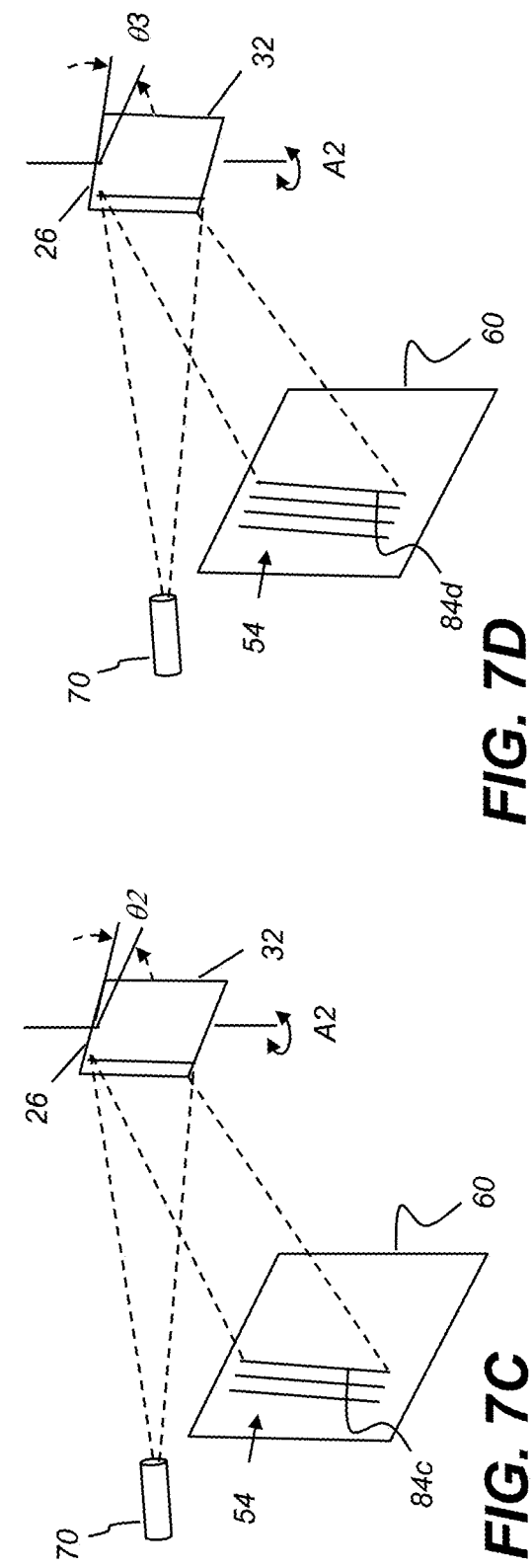
FIG. 7C
FIG. 7D

DENTAL SURFACE IMAGING APPARATUS USING LASER PROJECTION

CROSS REFERENCE TO RELATED APPLICATIONS

This application claims the benefit of and is a U.S. National Phase filing of PCT Application PCT/CN14/86635 filed Sep. 16, 2014 entitled "DENTAL SURFACE IMAGING APPARATUS USING LASER PROJECTION", in the name of Zhaohua Liu, et al, all of which are incorporated herein in their entirety.

TECHNICAL FIELD

The disclosure relates generally to the field of diagnostic imaging using structured light and more particularly relates to a method for three-dimensional imaging of the surface of teeth and other structures using fringe pattern projection from a scanned structured light source.

BACKGROUND

Fringe projection imaging uses patterned or structured light to obtain surface contour information for structures of various types. In fringe projection imaging, a pattern of lines of an interference fringe or grating is projected toward the surface of an object from a given direction. The projected pattern from the surface is then viewed from another direction as a contour image, taking advantage of triangulation in order to analyze surface information based on the appearance of contour lines. Phase shifting, in which the projected pattern is incrementally spatially shifted for obtaining additional measurements at the new locations, is typically applied as part of fringe projection imaging, used in order to complete the contour mapping of the surface and to increase overall resolution in the contour image.

Fringe projection imaging has been used effectively for surface contour imaging of solid, highly opaque objects and has been used for imaging the surface contours for some portions of the human body and for obtaining detailed data about skin structure. However, a number of technical obstacles complicate effective use of fringe projection imaging of the tooth. One particular challenge with dental surface imaging relates to tooth translucency. Translucent or semi-translucent materials in general are known to be particularly troublesome for fringe projection imaging. Subsurface scattering in translucent structures can reduce the overall signal-to-noise (S/N) ratio and shift the light intensity, causing inaccurate height data. Another problem relates to high levels of reflection for various tooth surfaces. Highly reflective materials, particularly hollowed reflective structures, can effectively reduce the dynamic range of this type of imaging.

From an optics perspective, the structure of the tooth itself presents a number of additional challenges for fringe projection imaging. As noted earlier, light penetrating beneath the surface of the tooth tends to undergo significant scattering within the translucent tooth material. Moreover, reflection from opaque features beneath the tooth surface can also occur, adding noise that degrades the sensed signal and thus further complicating the task of tooth surface analysis.

One corrective measure that has been attempted to make fringe projection workable for contour imaging of the tooth is application of a coating that changes the reflective characteristics of the tooth surface itself. Here, to compensate for problems caused by the relative translucence of the tooth, a number of conventional tooth contour imaging systems apply a paint or reflective powder to the tooth surface prior to surface contour imaging. For the purposes of fringe projection imaging, this added step enhances the opacity of the tooth and eliminates or reduces the scattered light effects noted earlier. However, there are drawbacks to this type of approach. The step of applying a coating powder or liquid adds cost and time to the tooth contour imaging process. Because the thickness of the coating layer is often non-uniform over the entire tooth surface, measurement errors readily result. More importantly, the applied coating, while it facilitates contour imaging, can tend to mask other problems with the tooth and can thus reduce the overall amount of information that can be obtained.

Even where a coating or other type of surface conditioning of the tooth is used, however, results can be disappointing due to the pronounced contours of the tooth surface. It can be difficult to provide sufficient amounts of light onto, and sense light reflected back from, all of the tooth surfaces. The different surfaces of the tooth can be oriented at 90 degrees relative to each other, making it difficult to direct enough light for accurately imaging all parts of the tooth. Further, it is difficult to project, from a camera that is compact enough to fit into the patient's mouth, a pattern that is sharply focused onto the tooth surface.

There have been a number of attempts to adapt structured light surface-profiling techniques to the problems of tooth structure imaging. For example, U.S. Pat. No. 5,372,502 entitled "Optical Probe and Method for the Three-Dimensional Surveying of Teeth" to Massen et al. describes the use of an LCD matrix to form patterns of stripes for projection onto the tooth surface. A similar approach is described in U.S. Patent Application Publication 2007/0086762 entitled "Front End for 3-D Imaging Camera" by O'Keefe et al. U.S. Pat. No. 7,312,924 entitled "Polarizing Multiplexer and Methods for Intra-Oral Scanning" to Trissel describes a method for profiling the tooth surface using triangularization and polarized light, but requiring application of a fluorescent coating for operation. Similarly, U.S. Pat. No. 6,885,464 entitled "3-D Camera for Recording Surface Structures, in Particular for Dental Purposes" to Pfeiffer et al. discloses a dental imaging apparatus using triangularization but also requiring the application of an opaque powder to the tooth surface for imaging. U.S. Pat. No. 6,885,464 to Pfeiffer et al. describes an intraoral camera that provides a group of light beams for imaging. Patent application WO 2011/145799 by Lim describes a 3-D scanner using scanned laser light.

It can be appreciated that an apparatus and method that provides accurate surface contour imaging of the tooth, without the need for applying an added coating or other conditioning of the tooth surface for this purpose, would help to speed reconstructive dentistry and could help to lower the inherent costs and inconvenience of conventional methods, such as those for obtaining a cast or other surface profile for a crown, implant, or other restorative structure.

SUMMARY

It is an object of the present invention to advance the art of dental imaging for intra-oral assessment. It is a feature of the present invention that it applies light that has good focus and is of sufficient brightness to the task of tooth contour imaging.

An advantage offered by the apparatus and method of the present invention relates to improved imaging of tooth surfaces and at lower cost over conventional contour imaging methods. Unlike conventional methods, for example, no powder or other opaque substance needs to be applied to the tooth as a preparatory step for contour imaging.

These objects are given only by way of illustrative example, and such objects may be exemplary of one or more embodiments of the invention, Other desirable objectives and advantages inherently achieved by the may occur or become apparent to those skilled in the art. The invention is defined by the appended claims.

According to one aspect of the disclosure, there is provided an intra-oral imaging apparatus for obtaining a contour image of a tooth, the apparatus comprising:
- a fringe pattern generator energizable to emit a fringe pattern illumination, the fringe pattern generator comprising:
  - (i) at least one structured light laser diode that is energizable to emit a patterned light beam;
  - (ii) at least one reflective element in the path of the emitted patterned light beam and actuable to rotate about an axis to scan the emitted patterned light beam along the tooth surface as fringe pattern illumination; a detector configured to acquire one or more images of the fringe pattern illumination from the tooth surface; and
- a control logic processor that is configured to control the fringe pattern generator for illuminating the tooth and to obtain and process the one or more images acquired by the detector.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other. Some exaggeration may be necessary in order to emphasize basic structural relationships or principles of operation. Some conventional components that would be needed for implementation of the described embodiments, such as support components used for providing power, for packaging, and for mounting and protecting system optics, for example, are not shown in the drawings in order to simplify description.

FIG. 5A is a plan view that shows a projected pattern.

FIGS. 7A-7D show a scanning apparatus having a mirror rotatable about a single axis and projecting a line at each of a number of angular increments.

DETAILED DESCRIPTION OF EXEMPLARY EMBODIMENTS

Figure 1A:
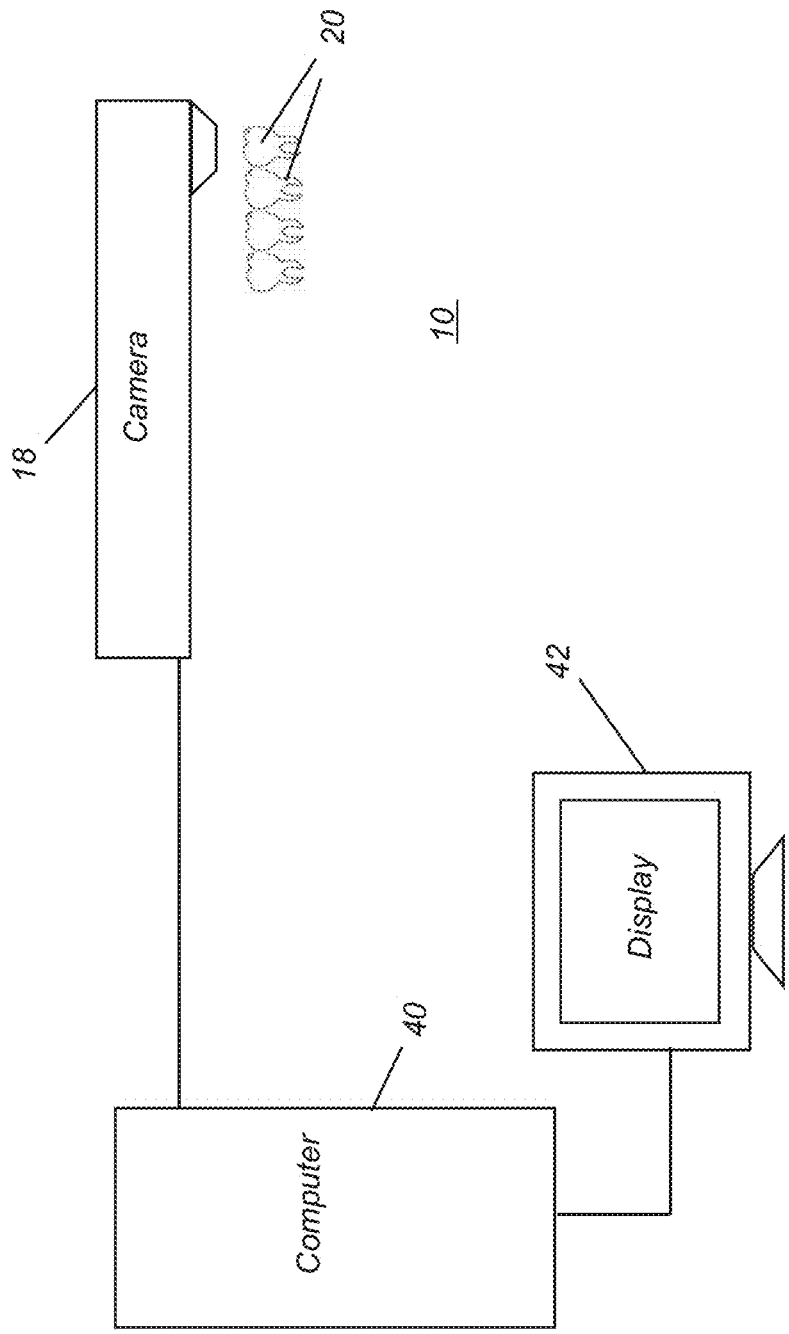
FIG. 1A shows an intra-oral imaging apparatus for contour imaging of teeth.

The following is a detailed description of exemplary embodiments, reference being made to the drawings in which the same reference numerals identify the same elements of structure in each of the several figures.

Where they are used in the context of the present disclosure, the terms "first", "second", and so on, do not necessarily denote any ordinal, sequential, or priority relation, but are simply used to more clearly distinguish one step, element, or set of elements from another, unless specified otherwise.

As used herein, the term "energizable" relates to a device or set of components that perform an indicated function upon receiving power and, optionally, upon receiving an enabling signal. The term "actuable" has its conventional meaning, relating to a device or component that is capable of effecting an action in response to a stimulus, such as in response to an electrical signal, for example.

In the context of the present disclosure, the term "fringe pattern illumination" is used to describe the type of structured illumination that is used for fringe projection imaging or "contour" imaging. The fringe pattern itself can include, as pattern features, one or more lines, circles, curves, or other geometric shapes that are distributed over the area that is illuminated and that have a predetermined spatial and temporal frequency. One exemplary type of fringe pattern that is used for contour imaging is a pattern of evenly spaced lines of light projected onto the surface of interest.

Two lines of light, portions of a line of light, or other features in a pattern of structured illumination can be considered to be substantially "dimensionally uniform" when their line width is the same over the length of the line to within no more than ±15 percent. As is described in more detail subsequently, dimensional uniformity of the pattern of structured illumination is used to maintain a uniform spatial frequency.

In the context of the present disclosure, a line can be considered to be a curved line if its radius of curvature is smaller than the image length or width dimension.

The term "structured light laser" refers to a solid-state laser light emitter that includes integral optics for emitting a patterned light beam that projects a pattern of light onto a surface, rather than scanning the single, thin laser beam that is generated by the laser itself and that directs all of the emitted light in parallel along an optical axis. One familiar type of structured light laser is the "line laser", a laser with optics that include one or more optical elements that condition the beam to project a line output instead of a point output. The optical elements of a structured light laser are typically integrated with the laser.

A patterned light beam from a laser light source projects an output beam having a two-directional pattern when considered in cross-section through the optical axis. The patterned light beam projects a visible geometric pattern onto a surface positioned along the optical axis in the path of the beam, where the surface is at least partially orthogonal to the optical axis. The projected geometric pattern extends away from the optical axis of the laser in at least one direction that is not parallel to, or orthogonal to, the optical axis. A patterned light beam can provide a pattern as a line, as shown in figures described subsequently. Alternately, the patterned light beam can provide a pattern as a set of multiple lines, or as a curve or set of multiple curves, or as a pattern of dots of light, for example.

In the context of the present disclosure, the term "optics" is used generally to refer to lenses and other refractive, diffractive, and reflective components used for shaping a light beam.

As was noted earlier in the background section, conventional approaches for fringe projection imaging often yield disappointing results for tooth tissue for a number of reasons. Apparatus and methods of the present invention address the problems of obtaining images of the tooth when using fringe projection imaging with fringe pattern illumination by using a structured light source and single-axis scanning method for fringe pattern generation and detection. Techniques of the present disclosure improve light delivery to the highly contoured tooth surface.

Figure 1B:
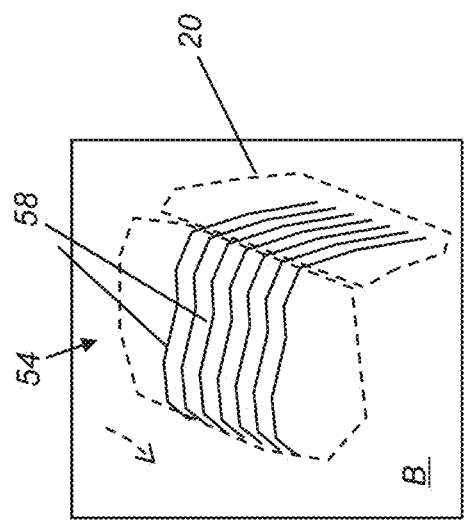
FIG. 1B shows using the camera to obtain a fringe pattern for contour imaging of teeth.
Figure 1B:
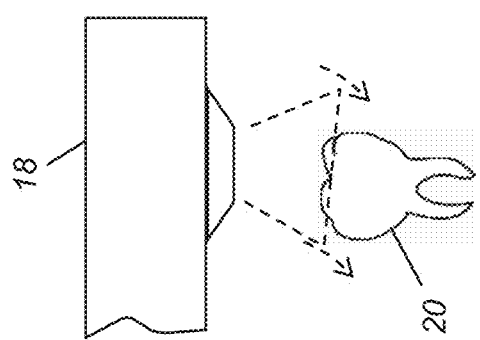

Referring to FIG. 1A, there is shown an intra-oral imaging apparatus 10 for contour imaging of one or more teeth 20 that includes an intraoral camera 18 the form of a probe. The camera 18 communicates, over a wired or wireless data communication channel, with a computer 40 that obtains the images from the projected fringe pattern. Computer 40 processes the images and provides output image data that can be stored as a data tile and displayed on a display 42. As shown in FIG. 1B, camera 18 includes a projector that scans an emitted pattern 54 of lines 58 or other features along the surface of tooth 20 as shown in an inset B. Camera 18 then captures the image periodically during the scan in order to obtain multiple images that can be combined to show contour information about the tooth surface. The contour imaging components of the present disclosure can be incorporated in a camera that also provides standard imaging using reflectance images or fluorescence imaging. According to an embodiment of the present disclosure, the scan of the emitted patterned light beam along the tooth surface is continuous, so that camera 18 is actuated at regular intervals to obtain successive images of the projected line. According to an alternate embodiment of the present disclosure, an indexing or stepped sequence is employed, in which the scan pattern 54 is formed by capture of successive images, each image acquired where the pattern projection is stopped for a short interval at each of a succession of evenly spaced positions. Thus, for the example scan pattern 54 of FIG. 1B, each line 58 is separately projected and imaged at a different time, such as 30 msec apart, and the images are registered to each other and combined.

Figure 2:
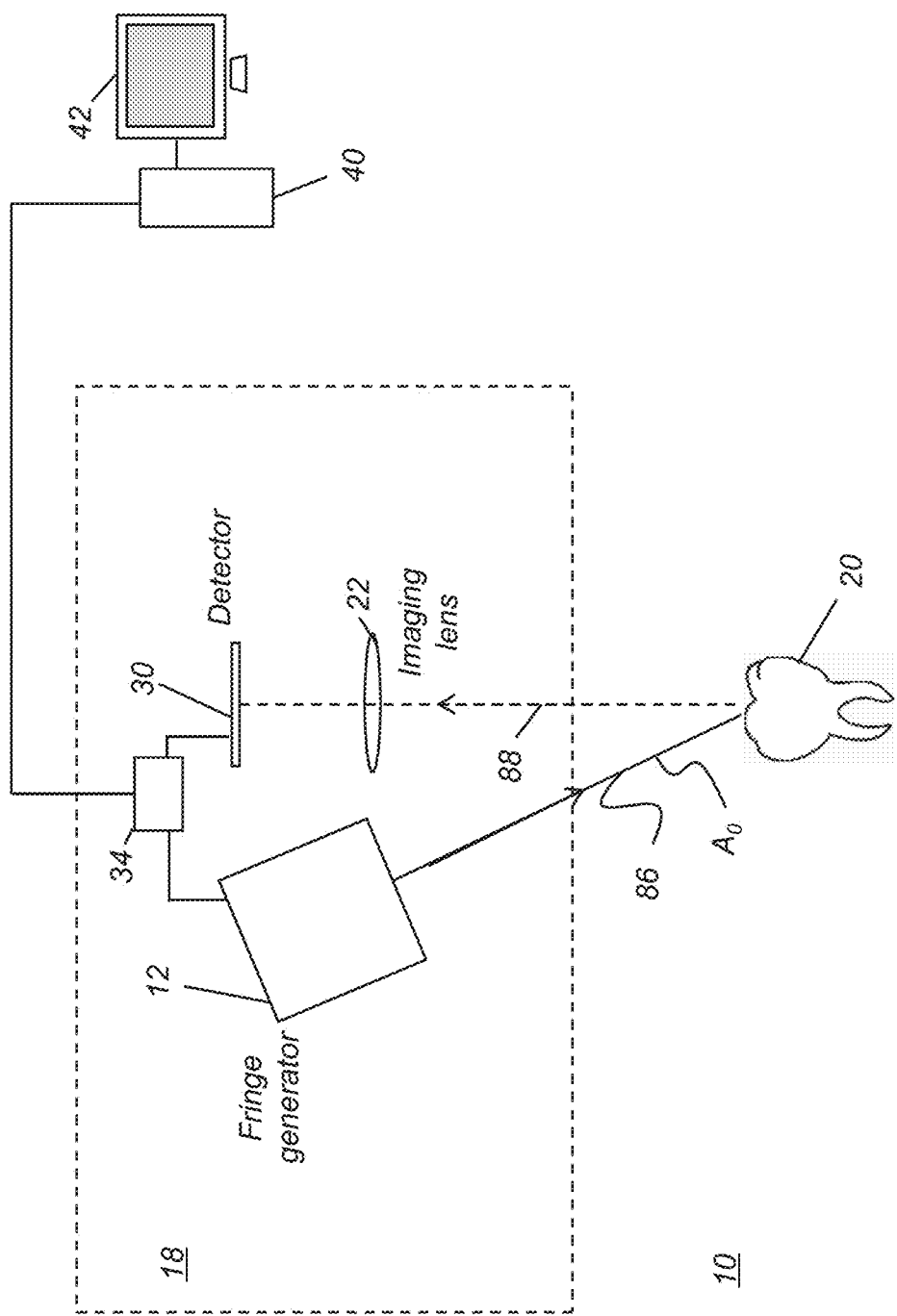
FIG. 2 is a schematic block diagram that shows an intra-oral imaging apparatus according to an embodiment of the present disclosure, including components of the camera.

Referring to the schematic block diagram of FIG. 2, there is shown in more detail an embodiment of an intra-oral imaging apparatus 10 for obtaining surface contour information from a tooth 20 using structured light illumination. In camera 18, a fringe pattern generator 12 is energized to form the structured light as a fringe pattern illumination and project the structured light thus formed as incident light toward tooth 20 having a beam direction or optical axis $A_0$ along an illumination path 86. The patterned light is scanned along the tooth 20 surface. Light reflected and scattered from tooth 20 is provided to a detector 30, through an imaging lens 22. Detector 30 is disposed along a detection path 88, at the image plane of imaging lens 22. A control logic processor 34 accepts feedback information from detector 30 and, in response to this and other data, is actuable to effect the operation of pattern generator 12 such as to change the position of the projected image and to capture the image periodically as described in more detail subsequently.

One function of control logic processor 34 for fringe projection imaging is to incrementally shift the position of the fringe pattern from fringe generator 12 and to trigger the detector 30 to capture images in synchronous manner. Two basic modes can be used for fringe pattern illumination:

(i) Continuous scan. The fringe pattern can be continuously scanned, with captures timed for increments along the scan.

(ii) Start-stop scan. Alternately, a start-stop timing arrangement can be provided so that incremental movement of the scanned patterned light source stops the light source momentarily at specific positions, capturing an image at each position.

The captured images are then registered to each other and combined to form a pattern, such as that shown in FIG. 5A, that is used to calculate three-dimensional information about the tooth surface. For the fringe projection method, multiple images are needed, taken in rapid succession and with the camera in a fixed position relative to the object (tooth), in order to provide enough information for calculating three-dimensional information about the object. For either mode (i) or (ii) above, the relative positions of the fringes for the projected images are incrementally shifted according to a pre-determined fringe spatial period and time period, using techniques that are familiar to those skilled in the contour imaging arts. To obtain the pattern, the separate images are registered to each other, then combined.

Control logic processor 34 can be a computer, microprocessor, or other dedicated logic processing apparatus that executes programmed instructions. Control logic processor 34 is in signal communication with computer 40 that has a display 42. Computer 40 performs the image processing functions that utilize the data obtained by control logic processor 34 to provide images showing the surface contour and features of tooth 20. It should be noted that various control logic and imaging functions can be performed by either control logic processor 34 or computer 40 or can be shared between these control logic devices, Additional computer devices (e.g., local or remote) can alternately be used to support various computational functions for contour analysis. The contour analysis itself can be implemented in any of a number of ways, using techniques familiar to those skilled in the 3-D imaging arts.

Figure 3:
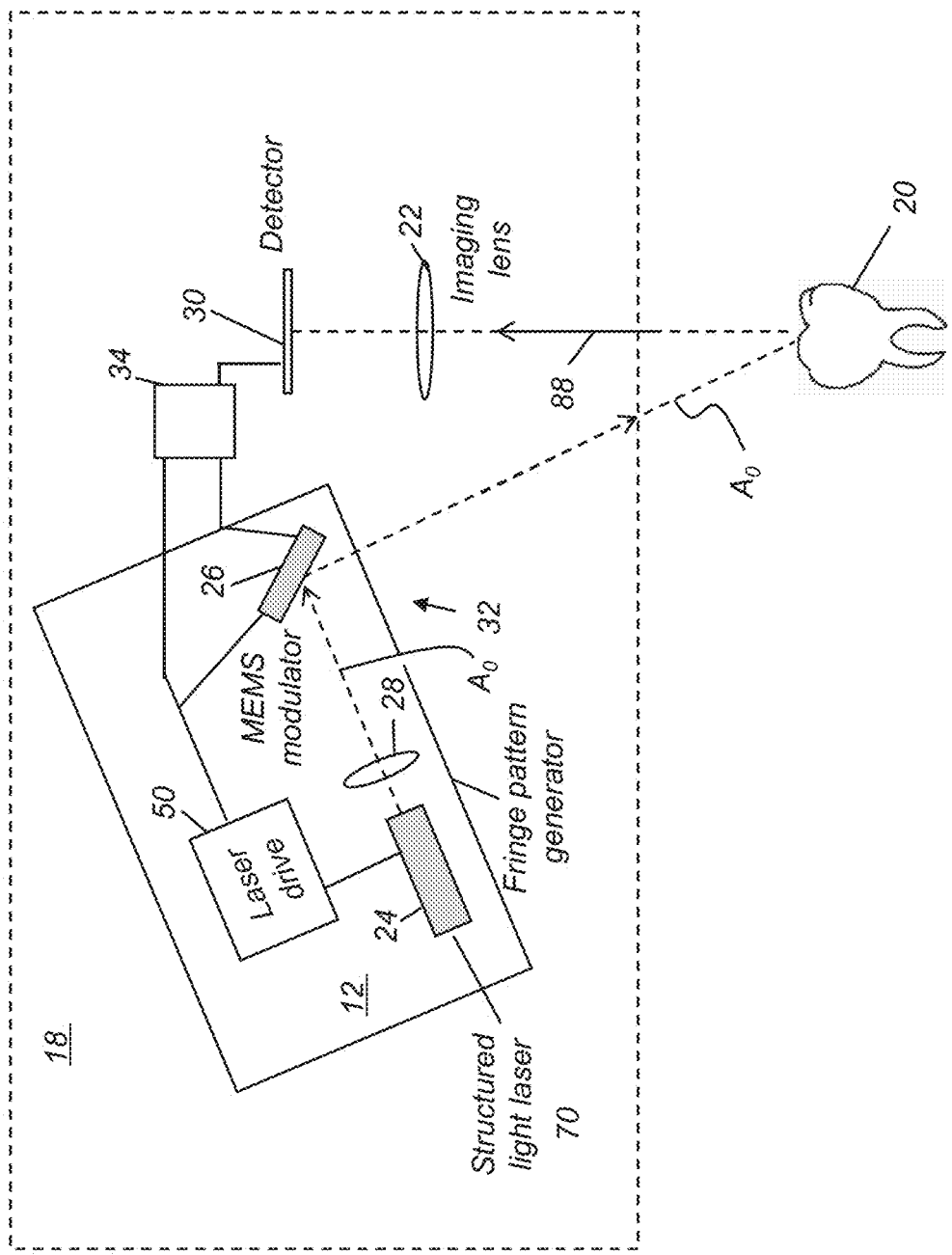
FIG. 3 is a schematic block diagram that shows an intra-oral imaging apparatus, including components of the camera fringe generator.

The schematic block diagram of FIG. 3 shows fringe pattern generator 12 components of camera 18 in more detail. A structured light laser 70 is energizable to emit a patterned laser light beam along optical axis $A_0$ through optional beam shaping optics 28, represented schematically as a lens in FIG. 3, to a reflective scanning element 32 such as a MEMS (Microelectromechanical systems) modulator 26. An integrated lens, which may be provided as part of a laser diode 24, can provide the function of laser-shaping optics 28 in structured light laser 70. The light-shaping optics can be integral to the laser diode; alternatively, an optical component for this light-shaping purpose may be separate from laser diode 24. A laser drive 50 controls laser actuation and timing, including turning structured light laser 70 on and off at appropriate points during the scan sequence when using start/stop mode (ii) described previously. Laser drive 50 is in signal communication with control logic processor 34. MEMS modulator 26, a uniaxial mirror according to an embodiment of the present disclosure, acts as reflective scanning element 32 and scans the laser beam along the surface of tooth 20 in the pattern needed for contour characterization. In one embodiment, the laser diode emits a line of laser light illumination in the range of 400-700 nm.

According to an embodiment of the present disclosure, the axis of rotation for the uniaxial scanning mirror is substantially parallel to the length dimension of the emitted laser beam line output, wherein substantially parallel means parallel to within no more than about ±20 degrees. For example, the laser beam line output can be perpendicular to the sheet holding FIG. 3. Alternately stated, the emitted line output is generated by scanning using a uniaxial scanning mirror that is energizable to rotate about an axis that is substantially orthogonal to the optical axis $A_O$ to direct the emitted light beam along the tooth 20 surface as fringe pattern illumination. In alternate embodiments, the axis of rotation for the uniaxial scanning mirror is not parallel to the length dimension of the emitted laser beam line output.

According to an alternate embodiment of the present disclosure, MEMS modulator 26 has an array of multiple reflective devices, such as an array of micromirrors. MEMS modulator 26 can control groups of micromirror devices to alter the projected pattern of illumination or its placement with this arrangement.

Figure 4:
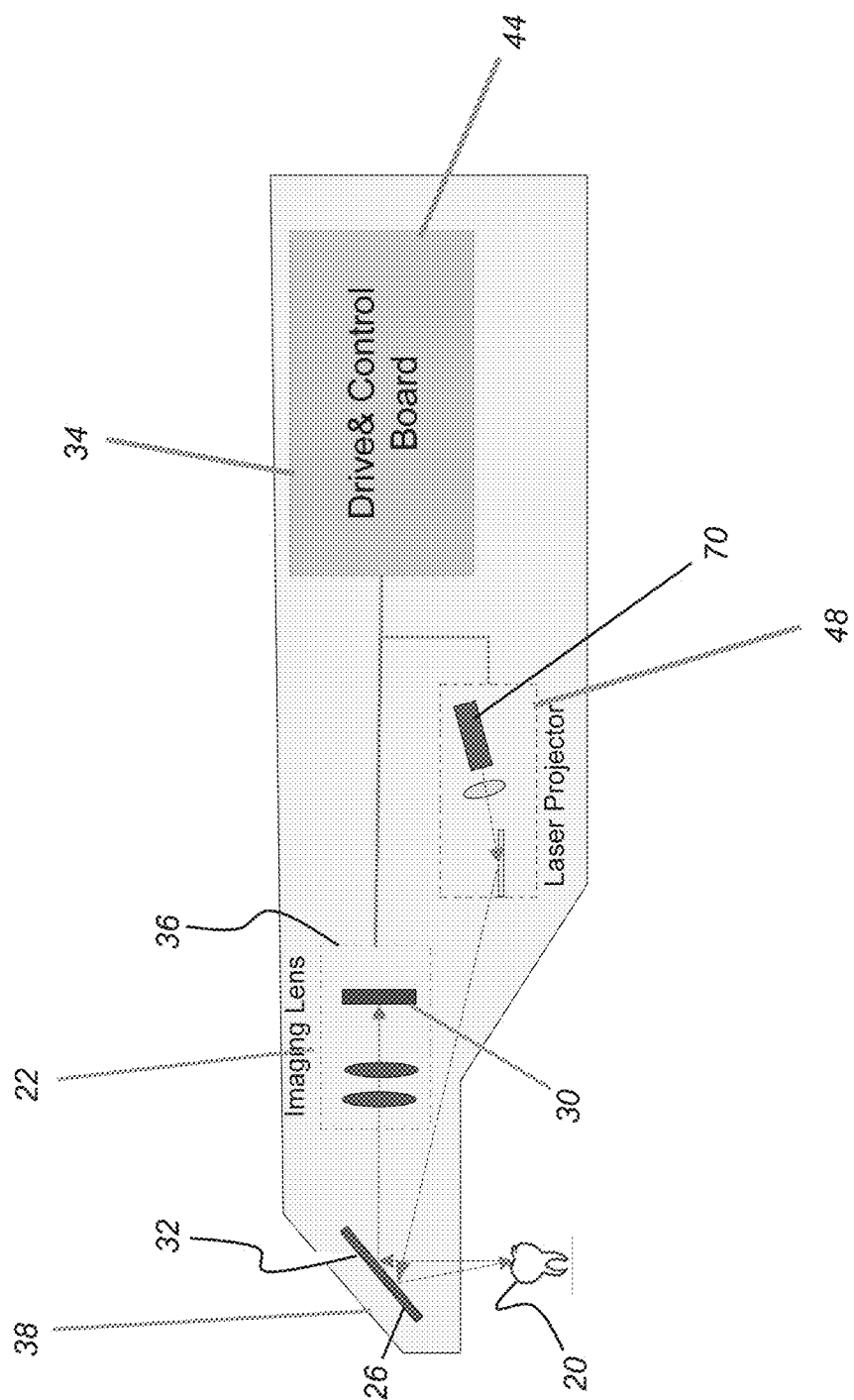
FIG. 4 is a cutaway view of the camera.

Camera 18 is a hand-held device that is inserted into the mouth of the patient. The cutaway side view of FIG. 4 shows components of camera 18 according to an embodiment of the present disclosure. The control logic processor 34 is part of an electronics board 44 that includes other support circuitry for power, enablement, and timing functions. A laser projector 48 includes structured light laser 70 and support circuitry and optics components for forming a pattern of illumination. A sensor assembly 36 contains detector 30 and related components. A probe 38 includes optical components that are placed over the tooth to be imaged and may include MEMS modulator 26 as reflective scanning element 32, as shown.

Figure 5B:
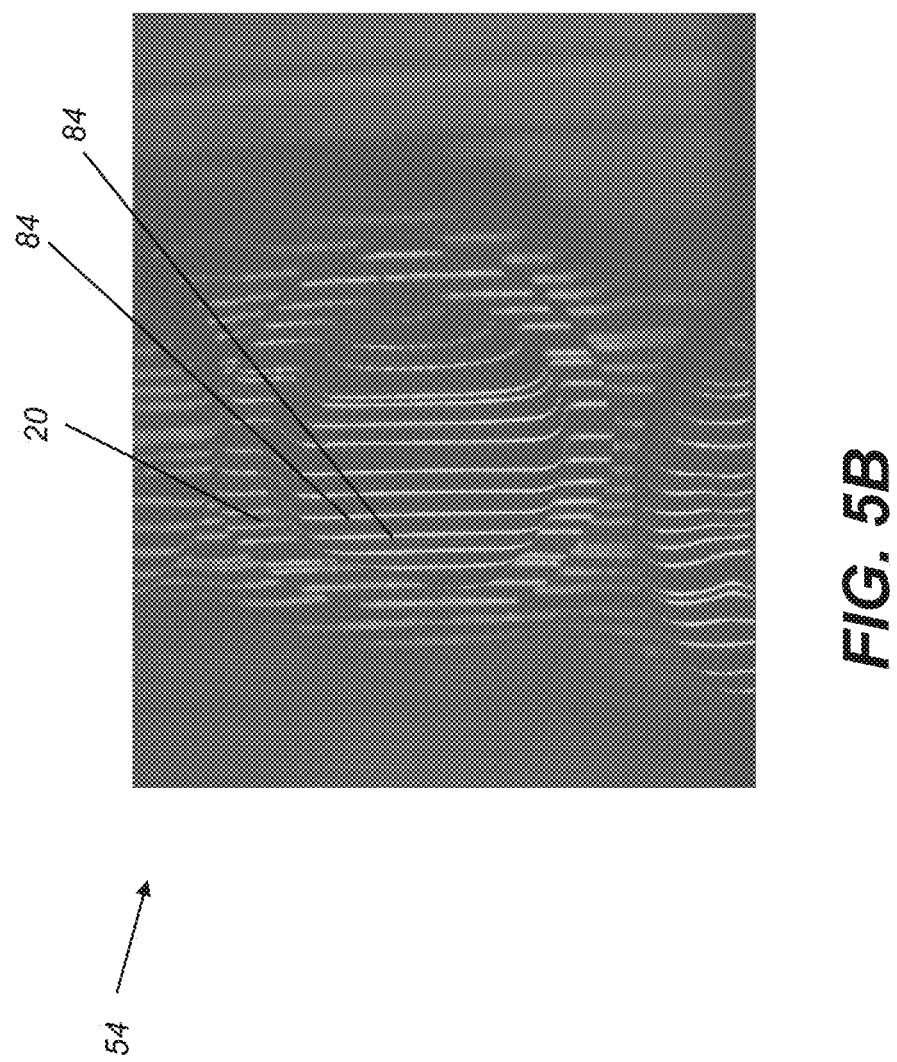
FIG. 5B shows a projected pattern on a model of a tooth.

The conventional fringe pattern imaging sequence projects a set of multiple, parallel lines of light onto the object. By way of example, FIG. 5A shows a conventional pattern 54 of lines 84 of illumination that are projected onto a tooth. Each line 84 has a uniform length dimension L and a very small beam width w. FIG. 5B shows one example of a tooth 20 illuminated by the scanned line pattern 54.

In conventional systems, pattern 54 can be formed in a number of ways, such as using a spatial light modulator that provides a two-dimensional pattern of light, so that multiple lines of illumination (as in FIG. 5A) are projected simultaneously. In conventional practice, laser light is not generally used for providing the lines of light or other illumination provided as a simultaneous pattern, since the laser is a point source. In order to form pattern 54 or other type of two-dimensional pattern with a point laser source, scanning along two axes is required. Scanning along a first axis forms the line of light, such as by scanning the laser beam rapidly from top to bottom using the arrangement of FIG. 5A; for forming a line, this first scan axis is orthogonal to the line length. Scanning along a second axis, orthogonal to the first axis, increments the position of the scan in order to form each successive line of illumination, parallel to the first line. The two mutually orthogonal scans are performed in succession, with one scan cycle considered as the scan movement along each axis that is needed for generating each separate line. Understandably, this bi-axial scan sequence complicates the design of the scanning optics where reflection is used to provide the scan function. Timing is also complex, since the scan activity that forms a line must occur within the capture cycle of the detector. That is, where a single mirror or other reflective surface is used, the mirror or reflective scan surface must be able to pivot or rotate with respect to two orthogonal axes. Individual images are obtained and combined, as described previously.

Figure 6:
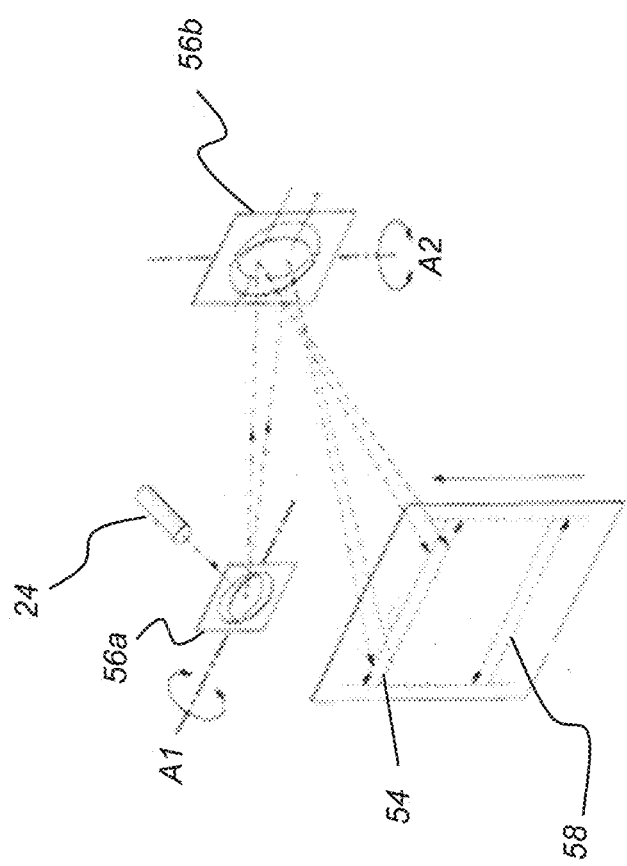
FIG. 6 shows a scanning apparatus having mirrors rotatable about orthogonal axes.

One alternative for providing the scanned parallel lines of FIG. 5A is to scan a point source using two reflective surfaces. FIG. 6 shows an alternate arrangement for forming pattern 54 of illumination, using reflection between a pair of uniaxial mirrors 56a and 56b that rotate with respect to mutually orthogonal axes. Laser diode 24 emits a beam toward mirror 56a which rotates with respect to an axis A1. Axis A1 is parallel to the length direction of lines 58 in pattern 54. The light is reflected from mirror 56a to mirror 5ob. Mirror 56b rotates on an axis A2 that is orthogonal to axis A1. As with the single mirror case, the FIG. 6 arrangement is complicated due to the use of the point source, laser diode 24. Mirrors 56a and 56b must be properly positioned and aligned in order to generate the appropriate illumination pattern 54. Precise timing is required where a point laser source is used with multiple mirrors that rotate on orthogonal axes.

To avoid the complexity of providing coordinated movement of a mirror about two orthogonal axes, embodiments of the present disclosure address the problem of generating pattern 54 using a single-axis reflector in combination with a line laser or other type of structured light laser 70. The line laser generates a line of laser light illumination from a laser source by using suitable optics at the laser light output. The emitted line of light extends in directions orthogonal to the optical axis $A_O$ as noted previously.

For embodiments of the present disclosure, pattern 54 of FIG. 5A can be projected using a single line laser source, with incremental shifts in reflection of the laser line along the tooth surface to capture multiple images and with combination of the multiple images that are thus obtained. In such an embodiment, a single line 84 is imaged at a time in a rapidly repeating sequence that projects and captures each line separately. The camera is held in fixed position during this imaging. The multiple single-line images that have been acquired are then combined to form what is shown in FIG. 5A as a composite image. In one form, multiple lines of illumination are successively captured and the images are registered and then combined to provide the multiline image pattern 54 of FIG. 5A. However, alternate arrangements for capturing multiple lines or other patterns of illumination are possible, as described in more detail subsequently.

The schematic diagrams of FIGS. 7A, 713, 7C, and 7D show structured light laser 70 as a line laser, directing a line of light toward a uniaxial mirror, reflective scanning element 32 of MEMS modulator 26. Reflective scanning element 32 reflects the line of light onto a surface 60 of the object to be imaged, such as the surface of a tooth. Incremental rotation of reflective scanning element 32 on axis A2 is synchronized with corresponding on/off cycling of structured light laser 70. Rotation to axis A2 angles $\theta 0$, $\theta 1$, $\theta 2$, $\theta 3$ successively, are shown in FIGS. 7A-7D. This sequence forms pattern 54 one line at a time, as shown by successive lines 84a, 84b, 84c, and 84d.

Scan Timing

Control and coordination of structured light laser 70 timing and reflective scanning element 32 rotation for fringe pattern illumination is performed by laser drive 50 (FIG. 3). It can be appreciated that a number of variations are possible to the general sequence described with reference to FIGS. 7A-7D. Timing of structured light laser 70 energization and of image capture from detector 30 can be adjusted appropriately for the imaging sequence. For example, it may be efficient to scan the tooth continuously one or more successive times, and obtain and group images in any order for processing, provided that a sufficient number of images are obtained for contour imaging calculations.

According to an embodiment of the present disclosure, the scan sequence described with reference to FIGS. 7A-7D is performed very rapidly, enabling a single image captured by detector 30 to include multiple lines 58, or even to include all of the projected lines 58 of pattern 54. For this sequence, the operator positions camera 18 near the tooth 20 to be imaged and issues the instruction to obtain a contour image for analysis. The scan sequence shown in FIGS. 7A-7D executes very quickly, so that a single image of the tooth with numerous projected lines of illumination is acquired with the camera 18 at that position. Thus, for example, a single image capture can include 50 or more scan lines, for example, as a result of a single instruction. Alternately, multiple images can be obtained, so that each captured image has a single projected line or has two or more projected lines 58 of illumination. Where multiple images are needed, methods for multiple image registration are familiar to those skilled in the imaging arts.

The sequence shown in FIGS. 7A-7D can be executed to form adjacent lines 58; however, lines 58 can be generated in any order, so that two lines 58 that are adjacent in space may not have been formed in temporal succession. According to an embodiment of the present disclosure, lines 58 are generated in a randomized manner, so that lines 1, 2 . . . n are not generated in succession. This type of arrangement can be used to help reduce noise effects or to help compensate for patient movement, for example. According to an alternate embodiment of the present invention, every other line is generated and captured in a first image (for example, lines 1, 3, 5, 7 . . . (n−1)); then the series of alternate lines is generated and captured in a second image (for example, lines 2, 4, 6, 8, . . . (n)). The first and second images can then be registered to each other and combined and used for contour image processing.

Figure 8:
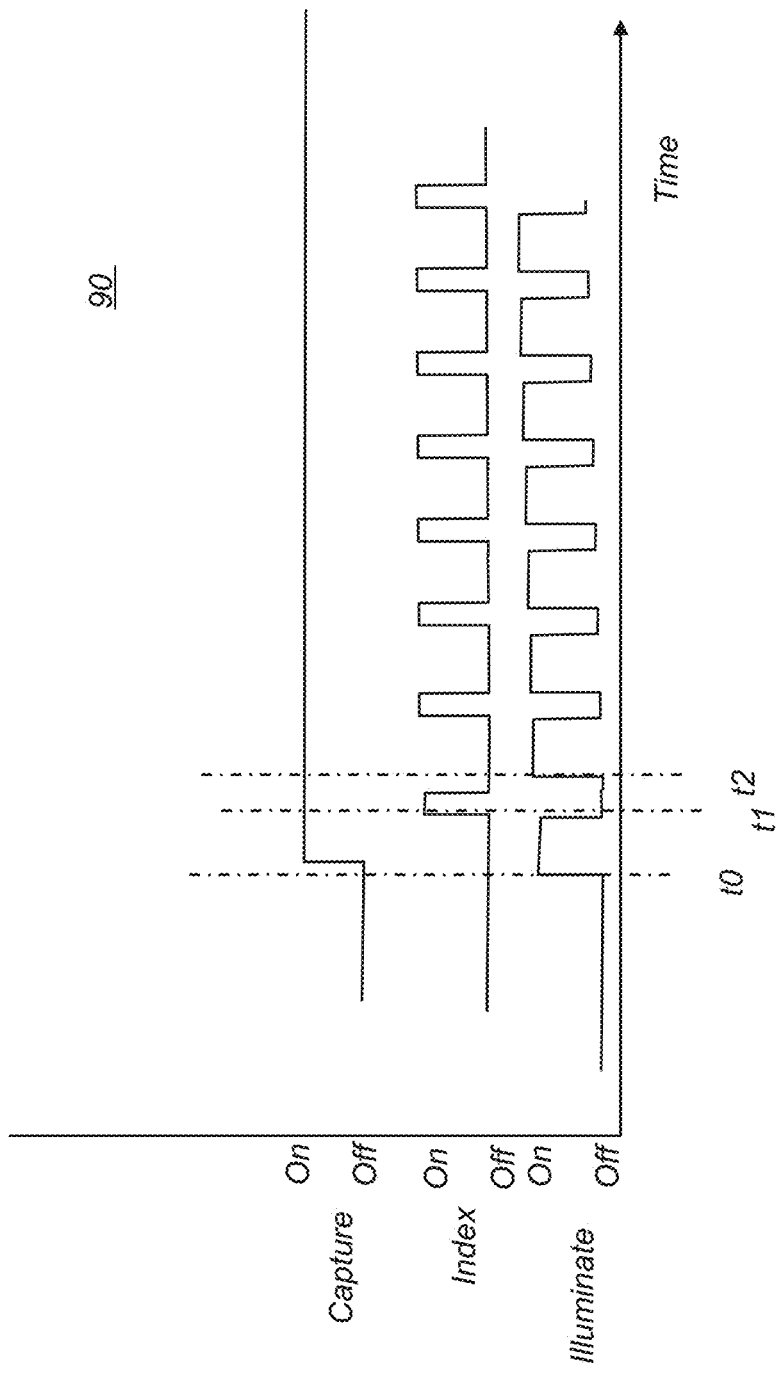
FIG. 8 is a timing diagram that shows relative timing of image capture, mirror indexing, and laser illumination to form each line during pattern generation and imaging.

The timing diagram of FIG. 8 shows relative timing of image capture, mirror indexing, and laser illumination to form each line 58 during pattern generation and imaging. In a timing diagram 90, at a time t0, the laser is energized (On) and the laser line illuminates reflective scanning element 32; image capture is enabled (On) when the laser has been energized and the first line 58 is recorded. At a time t1, the laser is de-energized (Off) and MEMS modulator 26 is actuated by an Index signal (On) to rotate reflective scanning element 32 to its the position for forming the next line 58. At a time t2, the laser is re-energized to provide illumination for the next line. This same cycle repeats as many times as needed in order to form the pattern 54 of lines 58 for fringe pattern illumination.

According to an alternate embodiment of the present disclosure, the image capture sequence includes logic for detecting patient movement during the scan imaging sequence. Movement detection can be performed in a number of ways, including by repeated projection and capture of the same image content during the imaging cycle, for example.

Figure 9:
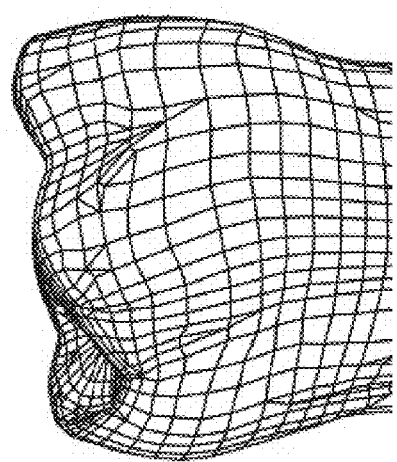
FIG. 9 shows an exemplary tooth surface computed using fringe pattern results.

Based on the acquired images of the projected pattern 54, computer 40 then generates contour information for the tooth, as shown in the contour image example of FIG. 9.

Detector 30 is configured to acquire one or more images of the fringe pattern illumination from the tooth surface. Detectors 30 in embodiments described herein can be any of a number of types of image sensing array. Detector 30 can be a CMOS (complementary metal oxide semiconductor) imaging sensor or a CCD (charge-coupled device) sensor, for example. The camera optics can also include filters, polarizers, and other components in the projection or detection paths.

In one embodiment of the present invention, the imaging apparatus is packaged in the form of a hand-held probe that can be easily positioned within the patient's mouth with little or no discomfort.

It should be noted that structured light laser 70 has the form of a line laser due to laser shaping optics, typically integral to the laser package. The laser shaping optics can include various types of lenses, apertures, and other devices for conditioning the shape of the laser output beam. According to an alternate embodiment of the present disclosure, laser-shaping optics are used to form the laser beam into a pattern that includes changes in width dimension over the length of the beam. The beam can also be interrupted over its length, such as to generate a dashed line or other pattern, for example.

Figure 10:
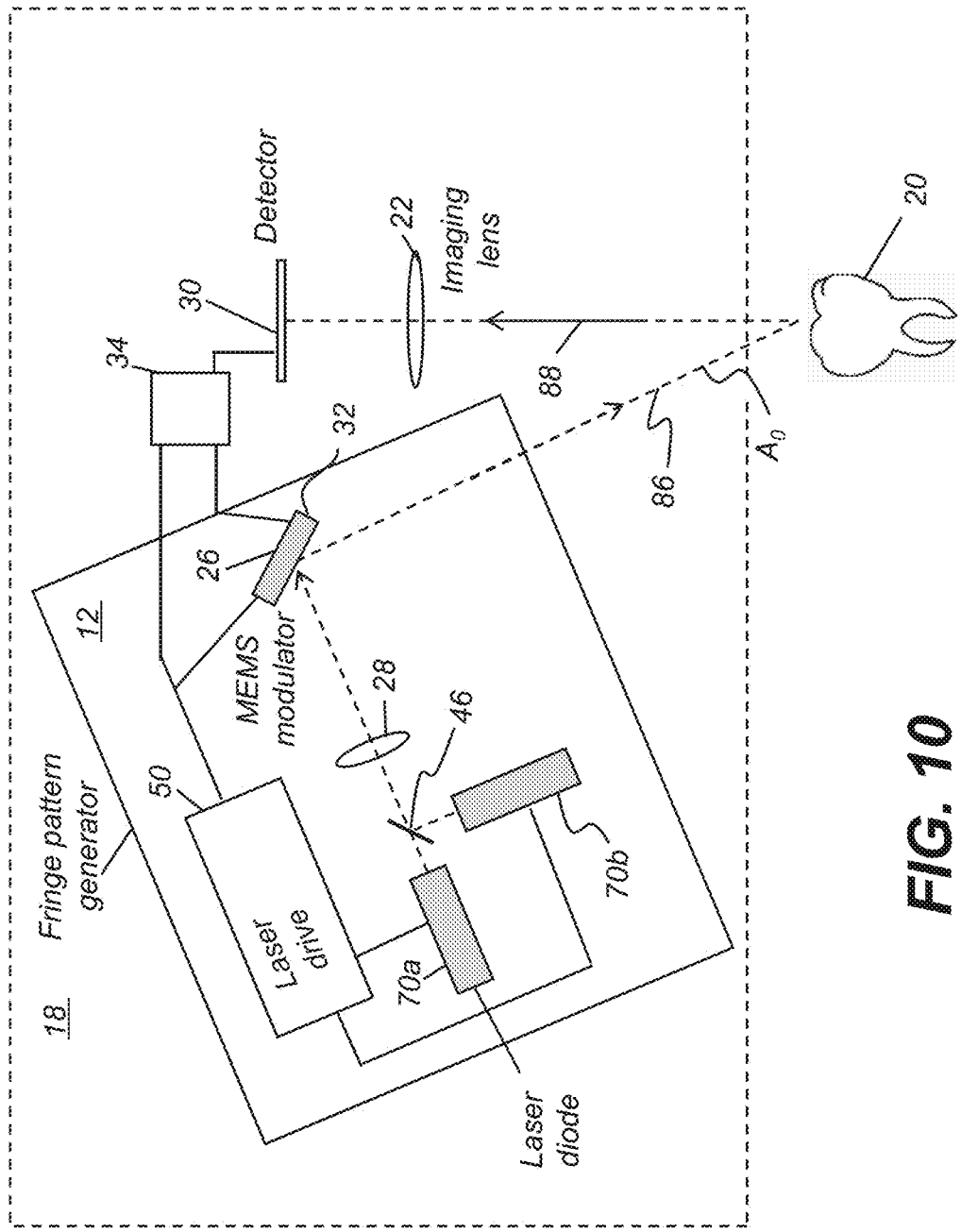
FIG. 10 is a schematic diagram that shows an intra-oral imaging apparatus according to an alternate embodiment of the present disclosure.

According to an alternate embodiment of the present invention, multiple laser diode light sources can be used to provide illumination for surface contour imaging. Referring to FIG. 10, there is shown an embodiment of camera 18 having two structured light lasers 70a and 70b that can be energized alternately or simultaneously to provide patterned illumination to illumination path 86 with different characteristics. Laser drive 50 energizes structured light lasers 70a and 70b, alternately or simultaneously, to direct their respective lines or other patterns of light towards MEMS modulator 26 through a beamsplitter 46. In the embodiment shown in FIG. 10, beamsplitter 46 transmits light wavelengths emitted from laser 70a and reflects light from laser 70b. More than two laser diodes can be combined in similar fashion in order to provide color light or other useful characteristics for imaging.

Figure 11A:
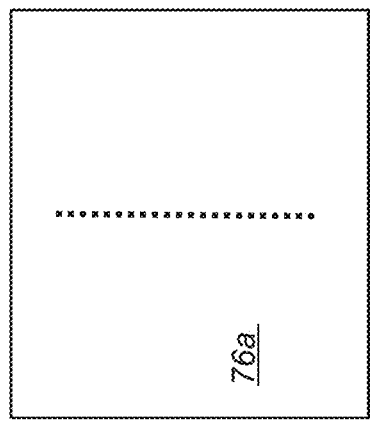
FIGS. 11A-11E show alternate patterns that can be used for fringe pattern projection according to embodiments of the present disclosure.
Figure 11B:
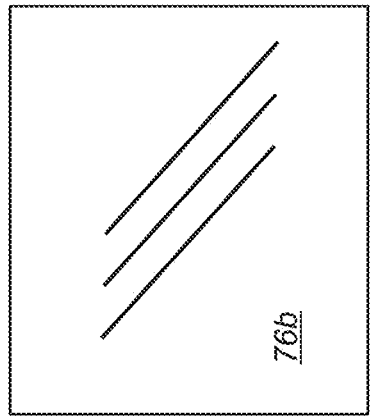
Figure 11C:
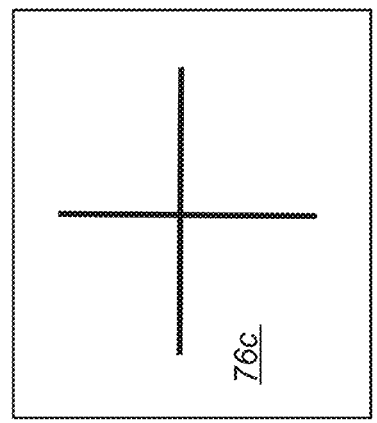
Figure 11D:
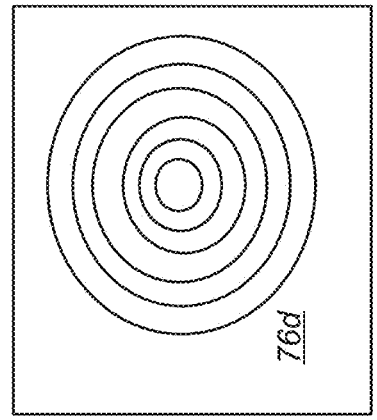
Figure 11E:
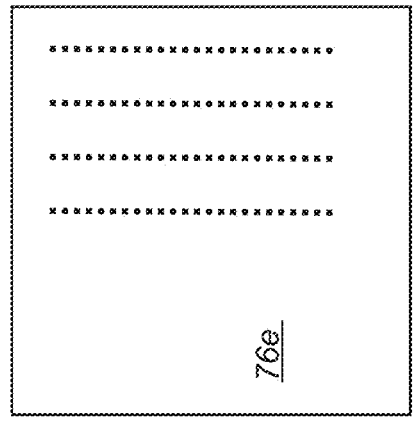

Structured light laser 70 can provide an output beam that provides a single line alight along the projection surface, as described herein with reference to FIG. 3. However, other patterns are possible and are available with some types of structured light laser diodes. FIGS. 11A-11D show a few of the many possible projection patterns that are available. FIG. 11A shows a dotted line pattern 76a. FIG. 11B shows a pattern 76b having multiple lines projected simultaneously. FIG. 11C shows a cross pattern 76c with two orthogonal lines. FIG. 11D shows a pattern 76d of concentric circles, an example of a pattern with curved lines; here, segments of the circles can be considered to be piece-wise parallel. FIG. 11E shows a two-dimensional pattern 76e having two or more dots.

The surface contour image that is obtained using the apparatus and methods of the present invention can be processed and used in a number of ways. Contour data can be displayed and can be input into a system for processing and generating a restorative structure or can be used to verify the work of a lab technician or other fabricator of a dental appliance. This method can be used as part of a system or procedure that reduces or eliminates the need for obtaining impressions under some conditions, reducing the overall expense of dental care. Thus, the imaging performed using this method and apparatus can help to achieve superior fitting prosthetic devices that need little or no adjustment or fitting by the dentist. From another aspect, the apparatus and method of the present invention can be used for long-term tracking of tooth, support structure, and bite conditions, helping to diagnose and prevent more serious health problems. Overall, the data generated using this system can be used to help improve communication between patient and dentist and between the dentist, staff, and lab facilities.

Advantageously, the apparatus and method of the present invention provide an intra-oral imaging system for 3-D imaging of teeth and other dental features without requiring the use of a special powder or application of some other temporary coating for the tooth surface. The system offers high resolution, in the 25-50 μm range in one embodiment.

Consistent with an embodiment of the present invention, a computer program utilizes stored instructions that perform on image data that is accessed from an electronic memory. As can be appreciated by those skilled in the image processing arts, a computer program for operating the imaging system in an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the Internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer is also considered to be a type of memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

In one embodiment, an intra-oral imaging apparatus to obtain a contour image of a tooth can include a fringe pattern generator energizable to emit a fringe pattern illumination, the fringe pattern generator including (i) at least one structured light laser that is energizable to emit a patterned light beam; (ii) at least one reflective element in the path of the emitted patterned light beam and actuable to move to scan the emitted patterned light beam repeatedly offset in at least one direction toward the tooth surface as fringe pattern illumination; a detector configured to acquire one or more images of the fringe pattern illumination from the tooth surface; and a control logic processor that is configured to control the fringe pattern generator to illuminate the tooth and to obtain and process the one or more images acquired by the detector. In one embodiment, the least one reflective element can rotate, revolve or shift to scan the emitted patterned light beam.

While the invention has been illustrated with respect to one or more implementations, alterations and/or modifications can be made to the illustrated examples without departing from the spirit and scope of the appended claims. For example, reflective scanning element 32 (FIG. 3) can be a prism or other type of reflective component. In addition, while a particular feature of the invention can have been disclosed with respect to one of several implementations, such feature can be combined with one or more other features of the other implementations as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. The presently disclosed embodiments are therefore considered in all respects to be illustrative and not restrictive. Other embodiments of the invention will be apparent to those skilled in the art from consideration of the specification and practice of the invention disclosed herein. The scope of the invention is indicated by the appended claims, and all changes that come within the meaning and range of equivalents thereof are intended to be embraced therein.

What is claimed is:

1. An intra-oral imaging apparatus for obtaining a surface contour image of a tooth, the apparatus comprising:
   a structured light fringe pattern generator energizable to repeatedly emit a fringe pattern illumination, the fringe pattern generator comprising:
   (i) at least one structured light laser that is energizable to emit a patterned light beam;
   (ii) at least one reflective element in the path of the emitted patterned light beam and actuable to repeatedly rotate about an axis to reflect the emitted patterned light beam toward the tooth surface a plurality of times, wherein the repeated rotation and reflection of the patterned light beam in amalgamation forms the fringe pattern illumination that includes a plurality of patterned light beams;

a detector configured to acquire images of the fringe pattern illumination from the tooth surface; and a control logic processor that is configured to control the structured light fringe pattern generator to illuminate the tooth, where the relative position of the fringe pattern illumination is incrementally shifted according to a pre-determined fringe spatial period and time period, and to obtain and process the images acquired by the detector to generate the surface contour image.

2. The apparatus of claim 1 wherein the emitted patterned light beam forms a line on the tooth surface.

3. The apparatus of claim 1 wherein the emitted patterned light beam forms a two-dimensional pattern simultaneously having two or more substantially parallel lines or having two or more curved lines.

4. The apparatus of claim 3 wherein the emitted patterned light beam forms a two-dimensional pattern having two or more dots.

5. The apparatus of claim 1 wherein the reflective element is a microelectromechanical systems device or a prism, and wherein the detector comprises one of a CMOS detector and a CCD detector.

6. An intra-oral imaging apparatus for obtaining a contour image of a tooth, the apparatus comprising:
   a fringe pattern generator energizable to emit a fringe pattern illumination, the fringe pattern generator comprising:
   (i) at least a first laser diode that is energizable to emit a first light beam along an optical axis;
   (ii) optics in the path of the emitted first light beam from the first laser diode, wherein the optics shape the emitted first light beam to provide a line output, wherein the line extends in a direction that is orthogonal to the optical axis;
   (iii) a second laser diode that is energizable to emit a second light beam at a wavelength that differs from the wavelength of the first laser diode;
   (iv) a beamsplitter that is disposed to combine light from the shaped emitted first light beam and the second light beam from the first and second laser diodes, respectively, to form an emitted light beam; and
   (v) a reflective element in the path of the emitted line beam and energizable to rotate about an axis that is substantially orthogonal to the optical axis to repeatedly direct the emitted light beam along a tooth surface as the fringe pattern illumination;
   a detector configured to form one or more images of the fringe pattern illumination from the tooth surface; and
   a control logic processor that is configured to control the fringe pattern generator for illuminating the tooth and to obtain and process the one or more images acquired by the detector.

7. The apparatus of claim 6, where the reflective element is a microelectromechanical systems device or a prism, and where the optics comprise a lens.

8. A method for obtaining a surface contour image of a tooth, the method executed at least in part by a computer and comprising:
   energizing a structured light laser diode to emit a line light beam extending in one direction;
   repeatedly rotating at least one uniaxial reflective element in the path of the emitted line light beam about an axis to scan the line light beam along a tooth surface a plurality of times to generate a fringe pattern illumination comprising a plurality of spaced lines, where the relative position of the fringe pattern illumination is incrementally shifted according to a pre-determined fringe spatial period and time period;
   forming one or more images of the fringe pattern illumination from the tooth surface;
   analyzing the images of the fringe pattern illumination to derive tooth contour information; and
   displaying the tooth contour information according to the analysis.

9. The method of claim 8, where energizing a structured light laser diode to emit a patterned light beam comprises:
   energizing a second structured light laser diode to emit a light beam at a wavelength that differs from a wavelength of a light beam of a first structured light laser diode; and
   combining light beams from the first and second laser diodes using a beamsplitter to form the emitted patterned light beam.

* * * * *